United States Patent [19]

Mizuno et al.

[11] 4,266,081

[45] May 5, 1981

[54] PROCESS FOR PREPARATION OF PEROXIDES

[75] Inventors: Kenichi Mizuno, Ohtake; Hiroshi Iwasaki, Yamoguchi; Hirohiko Nambu, Ohtake, all of Japan

[73] Assignee: Mitsui Petrochemical Industries Ltd., Tokyo, Japan

[21] Appl. No.: 944,271

[22] Filed: Sep. 21, 1978

[30] Foreign Application Priority Data

Sep. 29, 1977 [JP] Japan ............................. 52/116028

[51] Int. Cl.$^3$ ............... C07C 179/093; C07C 179/06
[52] U.S. Cl. .................................. 568/578; 568/561; 568/563
[58] Field of Search ................ 568/561, 563, 578

[56] References Cited

U.S. PATENT DOCUMENTS

| | | | |
|---|---|---|---|
| 2,668,180 | 2/1954 | Boardman | 568/561 |
| 3,402,205 | 9/1968 | Gregory | 568/561 |
| 3,764,628 | 10/1973 | Gregorian et al. | 568/561 |
| 3,787,504 | 1/1974 | Peri et al. | 568/561 |

*Primary Examiner*—Werren B. Lone
*Attorney, Agent, or Firm*—Sherman & Shalloway

[57] ABSTRACT

A process for the preparation of peroxides by condensation reaction of a tertiary organic hydroperoxide with a tertiary alcohol, which is characterized in that zinc chloride is present as a catalyst in an amount of at least 1% by weight based on the tertiary alcohol, is disclosed. This process can be advantageously applied to continuous manufacture of peroxides, and according to this process, peroxides can be obtained in high yields.

14 Claims, No Drawings

PROCESS FOR PREPARATION OF PEROXIDES

BACKGROUND OF THE INVENTION (1) Field of the Invention:

This invention relates to a process for preparing peroxides in high yields. More particularly, the invention relates to a process for the preparation of peroxides which comprises condensing a tertiary organic hydroperoxide with a tertiary alcohol in the presence of a specific amount of zinc chloride as a catalyst.

(2) Description of the Prior Art:

A process for preparing a peroxide by reacting an organic hydroperoxide with a tertiary alcohol in the presence of a strong acid such as sulfuric acid or p-toluenesulfonic acid or a Friedel-Crafts catalyst such as boron trifluoride or aluminium chloride has been known from old as disclosed in the specification of U.S. Pat. No. 2,668,180. All the catalysts specifically disclosed in this specification have an activity of decomposing the starting hydroperoxide. Therefore, it is stipulated that the amount used of the catalyst should be reduced to a level as low as possible, namely 0.5% by weight or less based on the tertiary alcohol. However, when such decomposing catalyst is employed, even if the amount is restricted so strictly, it is difficult to prepare the intended peroxide in a high yield.

SUMMARY OF THE INVENTION

We found that among catalysts disclosed in the above-mentioned specification, zinc chloride is especially low in the hydroperoxide-decomposing activity and when zinc chloride is selected as the catalyst and is used in an amount much larger than the amount taught in the above-mentioned specification, the intended peroxide can be prepared in an unexpectedly high yield. Based on this finding, we have now completed this invention.

In accordance with a fundamental aspect of this invention, there is provided a process for the preparation of peroxides by condensation reaction of a tertiary organic hydroperoxide with a tertiary alcohol, said process being characterized in that zinc chloride is present as a catalyst in an amount of at least 1% by weight based on the tertiary alcohol.

In accordance with one preferred embodiment of this invention, there is provided a process for the preparation of peroxides which comprises continuously feeding into a reaction vessel a tertiary organic hydroperoxide and a tertiary alcohol in the form of a solution in a hydrocarbon, the amount of the tertiary alcohol being substantially stoichiometric to the hydroperoxide, continuously feeding in said reaction vessel zinc chloride in an amount of 2 to 100% by weight based on the tertiary alcohol in the form of an aqueous solution, conducting condensation reaction in said reaction vessel at a temperature of 30° to 100° C. for 15 minutes to 8 hours, continuously withdrawing the reaction mixture from said reaction vessel, and separating the formed peroxide from the reaction mixture.

DETAILED DESCRIPTION OF THE PREFERRED EMBODIMENTS

Any of tertiary organic hydroperoxides heretofore used for this reaction can be used in this invention. Among these tertiary organic hydroperoxides, there are preferably employed hydroperoxides represented by the following formula:

(1)

or

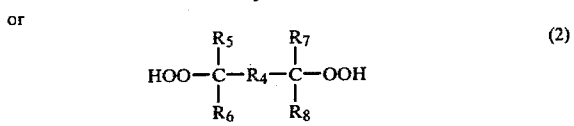

(2)

wherein $R_1$, $R_2$, $R_6$ and $R_8$ each stand for an aliphatic, alicyclic or aromatic monovalent hydrocarbon group having 1 to 13 carbon atoms, $R_3$, $R_5$ and $R_7$ each stand for an aliphatic monovalent hydrocarbon group having 1 to 5 carbon atoms, $R_4$ stands for an aliphatic, alicyclic or aromatic divalent hydrocarbon group, and these hydrocarbon groups may be substituted by a substituent not participating in the reaction, such as a chlorine atom, In the above formulae (1) and (2), it is preferred that each of $R_2$, $R_3$, $R_5$, $R_6$, $R_7$ and $R_8$ be a methyl group, $R_1$ be an aliphatic monovalent hydrocarbon group having 1 to 4 carbon atoms or an aromatic monovalent hydrocarbon group having 6 to 10 carbon atoms and $R_4$ be an aliphatic divalent hydrocarbon group having 1 to 2 carbon atoms or an aromatic divalent hydrocarbon group having 6 to 10 carbon atoms. As the aromatic hydrocarbon group having 6 to 10 carbon atoms, there can be mentioned, for example, phenyl, tolyl, cumyl and naphthyl groups.

As specific examples of such preferred tertiary organic hydroperoxide, there can be mentioned aliphatic hydroperoxides having 4 to 8 carbon atoms, such as tert-butyl hydroperoxide, tert-amyl hydroperoxide, 2,5-dimethyl-2,5-dihydroperoxyhexane and 2,5-dimethyl-2,5-dihydroperoxyhexyne-3, and aromatic hydroperoxides having 9 to 16 carbon atoms, such as cumene hydroperoxide, cymene hydroperoxide, m- and p-diisopropylbenzene monohydroperoxides, m- and p-diisopropylbenzene dihydroperoxides and isopropylnaphthalene hydroperoxide.

As the tertiary alcohol to be reacted with the above-mentioned tertiary organic hydroperoxide, any of aromatic tertiary alcohols and aliphatic tertiary alcohols customarily used for this reaction can be used in this invention. Among these tertiary alcohols, there are preferably employed tertiary alcohols represented by the following formula:

(3)

or

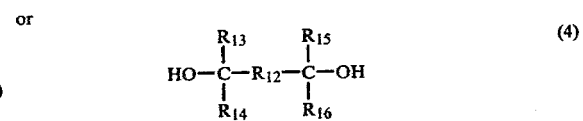

(4)

wherein $R_9$, $R_{10}$, $R_{13}$ and $R_{15}$ each stand for an aliphatic, alicyclic or aromatic monovalent hydrocarbon group having 1 to 13 carbon atoms, $R_{11}$, $R_{14}$ and $R_{16}$ each stand for an aliphatic monovalent hydrocarbon group having 1 to 5 carbon atoms, $R_{12}$ stands for an aliphatic divalent hydrocarbon group having 1 to 2 carbon atoms or an aromatic divalent hydrocarbon group having 6 to 10 carbon atoms, and these hydrocarbon groups may be substituted by a substituent not participating in the reaction, such as a chlorine atom.

In the above formulae (3) and (4), it is preferred that each of $R_{10}$, $R_{11}$, $R_{13}$, $R_{14}$, $R_{15}$ and $R_{16}$ be a methyl group.

As specific examples of such preferred tertiary alcohol, there can be mentioned aromatic tertiary alcohols having 9 to 13 carbon atoms, such as α,α-dimethylbenzyl alcohol, α,α-dimethyl-m- and p-methylbenzyl alcohols, α,α-dimethyl-m- and p-isopropylbenzyl alcohols, α,α'-dihydroxy-m- and p-diisopropylbenzenes, α,α-dimethyl-m- and p-chlorobenzyl alcohols, α,α-dimethyl-1-naphthyl alcohol and α,α-dimethyl-2-naphthyl alcohol, and aliphatic tertiary alcohols having 4 to 8 carbon atoms, such as tert-butyl alcohol, tert-amyl alcohol, 2,5-dimethyl-2,5dihydroxyhexane and 2,5-dimethyl-2,5-dihydroxyhexyne-3.

The mixing ratio of the organic hydroperoxide and tertiary alcohol to be reacted with each other is such that the amount of the alcoholic hydroxyl group of the tertiary alcohol is 0.8 to 1.5 equivalents, preferably 0.9 to 1.1 equivalents, especially preferably 1.0 to 1.1 equivalents, most preferably 1.0 equivalent, per equivalent of the hydroperoxide.

The most important feature of this invention is that zinc chloride is used as the catalyst in an amount of at least 1% by weight, preferably 2 to 100% by weight, especially preferably 3 to 50% by weight, based on the starting tertiary alcohol. Among catalysts heretofore used for the reaction between tertiary hydroperoxides and tertiary alcohols, zinc chloride is especially advantageous in that the activity of decomposing tertiary hydroperoxides is extremely low. When zinc chloride is used as the catalyst in the above-mentioned specific amount, the intended peroxide can be prepared at much higher conversion and selectivity than those attainable in the conventional process. When the amount used of zinc chloride is smaller than the above-mentioned amount, the reaction rate is low and the yield of the peroxide is reduced. When the amount used of zinc chloride is excessively increased, the selectivity to the intended peroxide is reduced owing to occurrence of side reactions. Therefore, it is preferred that the amount of zinc chloride used as the catalyst be adjusted within the above-mentioned range.

In this invention, zinc chloride can be made present in the reaction system in the form of an aqueous solution. For formation of such aqueous solution, water may be externally added or water formed by the condensation reaction may be utilized. In general, water is present in this aqueous solution in an amount of 0.5 to 5 moles, preferably 1 to 4 moles, per mole of zinc chloride. Accordingly, in the process of this invention, water formed as a by-product by the condensation reaction need not be completely removed, and good results can be obtained if only a part of such water is removed. As means for removal of water, there can be adopted known methods, for example, a method in which water is distilled by blowing an inert gas such as nitrogen, a method in which water is distilled under a reduced pressure, preferably under a pressure lower than 100 mmHg (absolute), and a method in which water is removed by azeotropic distillation with an appropriate hydrocarbon such as hexane, benzene or toluene. Since the reaction can be carried out in the presence of a small amount of water in the process of this invention as pointed out hereinbefore, when the reaction is conducted in a continuous manner, zinc chloride can be fed to a reaction vessel in the form of a liquid mixture with a small amount of water.

The reaction is carried out at a temperature of 30° to 100° C., preferably 40° to 80° C., especially preferably 40° to 70° C., for 0.1 to 10 hours, preferably 15 minutes to 8 hours. An inert diluent selected from aromatic hydrocarbons such as benzene, cumene and cymene, aliphatic hydrocarbons such as hexane and alicyclic hydrocarbons may be present in the reaction system.

In the process of this invention, the reaction is carried out batchwise while the starting compounds and catalyst are collectively charged in a reaction vessel. Further, in the process of this invention, the reaction is advantageously carried out in a continuous manner while feeding continuously the starting compounds and catalyst in a reaction vessel and withdrawing continuously the reaction mixture from the reaction vessel.

According to this invention, both the conversion of the starting compounds and the selectivity to the intended peroxide can be remarkably improved over the conversion and selectively attainable in the conventional process, and therefore, the intended peroxide can be obtained in an extremely high yield. Moreover, even if the catalyst-containing liquid mixture formed by the reaction is allowed to stand for a while, the loss of the peroxide by decomposition is very small, and therefore, any particular attention need not be paid to the post treatment and the post treatment can be performed very safely without any difficulty.

Removal of the catalyst from the reaction mixture can be accomplished very easily by a method comprising contacting the reaction mixture with a large quantity of water or a dilute aqueous solution of an alkali to extract the catalyst into the aqueous phase or a method comprising allowing the reaction mixture to stand still to separate the catalyst layer, then adding a small amount of an alkali to the oil layer and conducting filtration. From the reaction mixture left after removal of the catalyst, the peroxide can be isolated by customary procedures such as crystallization.

This invention will now be described in detail by reference to the following Examples that by no means limit the scope of the invention.

EXAMPLE 1

To 100 g of a cumene solution containing 42.2 g (278 millimoles) of cumene hydroperoxide (hereinafter referred to as "CHP") and 37.8 g (278 millimoles) of α,α-dimethylbenzyl alcohol (hereinafter referred to as "α-CA") was added 2.72 g (20 millimoles) of $ZnCl_2$, and the mixture was agitated at 60° C. for 3 hours under a current of nitrogen fed at a rate of 50 Nl/hour The amount of water contained in the resulting reaction mixture was 0.82 g (46 millimoles). It was found that 98.6% of the charged CHP was reacted and all of the reacted CHP was converted to dicumyl peroxide (hereinafter referred to as "DCP"), namely the selectively was 100%.

EXAMPLE 2

The reaction was carried out in the same manner as described in Example 1 except that $ZnCl_2$ as the catalyst was used in an amount of 0.68 g (5 millimoles). When the reaction was conducted for 4 hours, 97.6% of the charged CHP was reacted and all of the reacted CHP was converted to DCP. The amount of water contained in the resulting reaction mixture was 0.26 g (14 millimoles).

EXAMPLE 3

The reaction was carried out in the same manner as described in Example 1 except that the flow rate of the nitrogen current was changed to 30 Nl/hour. When the reaction was conducted for 5 hours, 96% of the charged CHP was reacted and 97% of the reacted CHP was converted to DCP. The amount of water contained in the resulting reaction mixture was 0.91 g (51 millimoles). When the reaction was further conducted for additional 1 hour, decomposition of DCP was not caused to occur at all.

EXAMPLE 4

To 100 g of a cumene solution containing 42.2 g (278 millimoles) of CHP and 37.8 g (278 millimoles) of α-CA was added 8.2 g (60 millimoles) of ZnCl$_2$, and the mixture was maintained at 60° C. under agitation. When the reaction was conducted for 30 minutes, 80% of the charged CHP was reacted and 91% of the reacted CHP was converted to DCP. The amount of water contained in the resulting reaction mixture was 4 g (222 millimoles).

EXAMPLE 5

To 50 g of a cumene solution containing 40 g of DCP was added 2.72 g (20 millimoles) of ZnCl$_2$, and 72 g of a cumene solution containing 30.4 g (200 millimoles) of CHP and 27.2 g (200 millimoles) of α-CA was gradually added to the above mixture over a period of 3 hours under agitation while flowing nitrogen at a rate of 30 Nl/hour. At the point of completion of the gradual addition, 83% of the charged CHP was reacted and all of the reacted CHP was converted to DCP.

EXAMPLE 6

A cumene solution containing CHP in an amount of 300 millimoles per 100 g and α-CA in an amount of 300 millimoles per 100 g was continuously fed at a rate of 60 ml/hour to a reaction vessel having an inner capacity of 150 ml and simultaneously, a 50% aqueous solution of ZnCl$_2$ was continuously fed at a rate of 1 ml/hour to the reaction vessel. The reaction was carried out while removing water by blowing nitrogen at a rate of 120 Nl/hour. The reaction mixture was withdrawn from the reaction vessel at a rate of 58 ml/hour so that the residence time was 2.5 hours. The diwthdrawn reaction mixture was allowed to stand still to separate it into catalyst and oil layers. When the oil layer was analyzed, it was found that the DCP concentration was 72.9% by weight and the unreacted CHP concentration was 2.4% by weight. Accordingly, it was confirmed that 95% of the charged CHP was reacted and 90% of the reacted CHP was converted to DCP. The catalyst layer was an aqueous solution of ZnCl$_2$ containing 27% by weight of water.

COMPARATIVE EXAMPLE 1

The reaction was carried out in the same manner as described in Example 1 except that the amount used of ZnCl$_2$ was changed to 0.136 g (1 millimole). The amount of CHP consumed for the reaction was 22% when the reaction was conducted for 4 hours, and even when the reaction was conducted for 8 hours, the amount of CHP consumed for the reaction was only 34%.

EXAMPLE 7

To 100 g of a toluene solution containing 42.2 g (278 millimoles) of CHP and 37.8 g (278 millimoles) of α-CA was added 2.72 g (20 millimoles) of ZnCl$_2$, and the mixture was maintained at 60° C. for 3 hours under agitation while flowing nitrogen at a rate of 50 Nl/hour. It was found that 99.2% of the charged CHP was reacted and 98.5% of the reacted CHP was converted to DCP.

EXAMPLES 8 to 10

The reaction was carried out in the same manner as described in Example 7 except that hexane, benzene or cymene was used as the solvent instead of toluene. Obtained results are shown in Table 1.

TABLE 1

| Example No. | Solvent | Reaction Time (hours) | Conversion (%) of CHP | Selectivity (%) to DCP |
|---|---|---|---|---|
| 8 | hexane | 3 | 98.3 | 98.7 |
| 9 | benzene | 3 | 98.6 | 99.1 |
| 10 | cymene | 3 | 97.1 | 100 |

EXAMPLE 11

To 100 g of a cumene solution containing 42.2 g (278 millimoles) of CHP and 41.7 g (278 millimoles) of α,α-dimethyltolylcarbinol was added 1.36 g (10 millimoles) of ZnCl$_2$, and the mixture was agitated at 60° C. for 3 hours under a current of nitrogen fed at a rate of 50 Nl/hour. It was found that 98.3% of the charged CHP was reacted and 98.5% of the reacted CHP was converted to cumylcymyl peroxide.

COMPARATIVE EXAMPLE 2

To 100 g of a cumene solution containing 42.2 g (278 millimoles) of CHP and 37.8 g (278 millimoles) of α-CA was added 3.8 g (20 millimoles) of p-toluene- sulfonic acid (monohydrate), and the mixture was agitated at 60° C. for 1.5 hours under a current of nitrogen fed at a rate of 50 Nl/hour. It was found that 99.2% of the charged CHP was reacted and 71% of the reacted CHP was coverted to DCP.

COMPARATIVE EXAMPLES 3 and 4

The reaction was carried out in the same manner as described in Comparative Example 2 except that the amount and kind of the catalyst were changed as indicated in Table 2. Obtained results are shown in Table 2.

TABLE 2

| Comparative Example No. | Catalyst Kind | Catalyst Amount (g) | Reaction Time (hours) | Conversion (%) of CHP | Selectivity (%) to DCP |
|---|---|---|---|---|---|
| 3 | p-toluene-sulfonic acid | 0.16 | 5 | 93.2 | 85.3 |
| 4 | H$_2$SO$_4$ | 0.12 | 4 | 95.3 | 80.5 |

EXAMPLE 12

A cumeme solution containing CHP in an amount of 300 millimoles per 100 g and α-CA in an amount of 300 millimoles per 100 g was continuously fed to a reaction vessel having an inner capacity of 300 ml at a rate of 150 ml/hour, and simultaneously, an 80% aqueous solution of ZnCl₂ was continuously fed to the reaction vessel at a rate of 2.6 g/hour. The reaction was carried out at 66° C. under a reduced pressure of 25 mm Hg while removing water. The reaction mixture was continuously withdrawn from the reaction vessel at a rate of 146 ml/hour so that the residence time was 1 hour. The withdrawn reaction mixture was allowed to stand still to separate it into catalyst and oil layers. When the oil layer was analyzed, it was found that the DCP concentration was 73% by weight and the unreacted CHP concentration was 2.3% by weight. Accordingly, it was confirmed that 95.5% of the charged CHP was reacted and 91% of the reacted CHP was converted to DCP. The catalyst layer was an aqueous solution of ZnCl₂ containing 25.3% by weight of water.

What we claim is:

1. A process for the preparation of peroxides by condensation reaction at a temperature of 30° to 100° C. of a tertiary organic hydroperoxide represented by the following formula:

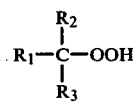

(1)

or

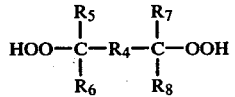

(2)

wherein $R_1$, $R_2$, $R_6$ and $R_8$ each stand for an aliphatic alicyclic or aromatic monovalent hydrocarbon group having 1 to 13 carbon atoms, $R_3$, $R_5$ and $R_7$ each stand for an aliphatic monovalent hydrocarbon group having 1 to 5 carbon atoms and $R_4$ stands for an aliphatic, alicyclic or aromatic divalent hydrocarbon group with a teritary alcohol represented by the following formula:

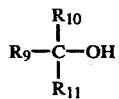

(3)

or

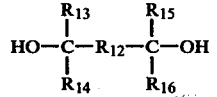

(4)

wherein $R_9$, $R_{10}$, $R_{13}$ and $R_{15}$ each stand for an aliphatic, alicyclic or aromatic monovalent hydrocarbon group having 1 to 13 carbon atoms, $R_{11}$, $R_{14}$ and $R_{16}$ each stand for an aliphatic monovalent hydrocarbon group having 1 to 5 carbon atoms, and $R_{12}$ stands for an aliphatic divalent hydrocarbon group having 1 to 2 carbon atoms or an aromatic divalent hydrocarbon group having 6 to 10 carbon atoms, said process being characterized in that zinc chloride is present as a catalyst in an amount of 2 to 100% by weight based on the tertiary alcohol, wherein the zinc chloride is present in the form of an aqueous solution containing from 1 to 4 moles of water per mole of zinc chloride.

2. A process according to claim 1 wherein zinc chloride is present in an amount of 3 to 50% by weight based on the tertiary alcohol.

3. A process according to claim 1 wherein said formulae, each of $R_2$, $R_3$, $R_5$, $R_6$, $R_7$ and $R_8$ is a methyl group, $R_1$ is an aliphatic monovalent hydrocarbon group having 1 to 4 carbon atoms or an aromatic monovalent hydrocarbon group having 6 to 10 carbon atoms and $R_4$ is an aliphatic divalent hydrocarbon group having 1 to 2 carbon atoms or an aromatic divalent hydrocarbon group having 6 to 10 carbon atoms.

4. A process according to claim 1 wherein the tertiary organic hydroperoxide is cumene hydroperoxide.

5. A process according to claim 1 wherein the tertiary alcohol is an aromatic tertiary alcohol.

6. A process according to claim 1 wherein the tertiary alcohol is an aliphatic tertiary alcohol.

7. A process according to claim 1 wherein in said formulae, each of $R_{10}$, $R_{11}$, $R_{13}$, $R_{14}$, $R_{15}$ and $R_{16}$ is a methyl group.

8. A process according to claim 1 wherein the tertiary alcohol is α,α-dimethylbenzyl alcohol.

9. A process according to claim 1 wherein the reaction is carried out in a hydrocarbon solvent under a current of an inert gas.

10. A process according to claim 1 wherein the reaction is carried out in a hydrocarbon solvent under a reduced pressure.

11. The process according to claim 1 wherein the amount of the alcoholic hydroxyl group of tertiary alcohol is 0.8 to 1.5 equivalents per equivalent of the hydroperoxide.

12. The process according to claim 1 wherein the condensation reaction is carried out for 0.1 to 10 hours.

13. The process according to claim 1 wherein the tertiary organic hydroperoxide is an aliphatic hydroperoxide having 4 to 8 carbon atoms or an aromatic hydroperoxide having 9 to 16 carbon atoms and the tertiary alcohol is an aromatic tertiary alcohol having 9 to 13 carbon atoms or an aliphatic tertiary alcohol having 4 to 8 carbon atoms, and wherein the amount of the tertiary alcohol is such that the amount of the alcoholic hydroxyl group contained therein is 0.8 to 1.5 equivalents per equivalent of the hydroperoxide.

14. A process for the preparation of peroxides which comprises continuously feeding into a reaction vessel a tertiary organic hydroperoxide and a tertiary alcohol in the form of a solution in a hydrocarbon, the amount of the tertiary alcohol being substantially stoichiometric to the hydroperoxide, continuously feeding in said reaction vessel zinc chloride in an amount of 2 to 100% by weight based on the tertiary alcohol in the form of an aqueous solution, conducting condensation reaction in said reaction vessel at a temperature of 30° to 100° C. for 15 minutes to 8 hours, continuously withdrawing the reaction mixture from said reaction vessel, and separating the formed peroxide from the reaction mixture.

* * * * *